United States Patent [19]

Chang et al.

[11] Patent Number: 5,580,731
[45] Date of Patent: Dec. 3, 1996

[54] N-4 MODIFIED PYRIMIDINE DEOXYNUCLEOTIDES AND OLIGONUCLEOTIDE PROBES SYNTHESIZED THEREWITH

[75] Inventors: Chu-An Chang, Piedmont; Michael S. Urdea, Alamo; Thomas Horn, Berkeley, all of Calif.

[73] Assignee: Chiron Corporation, Emeryville, Calif.

[21] Appl. No.: 296,793

[22] Filed: Aug. 25, 1994

[51] Int. Cl.$^6$ ............... C12Q 1/68; C12Q 1/70; C12P 19/34; C07H 21/04
[52] U.S. Cl. ............... 435/6; 435/5; 435/91.1; 536/24.3; 536/24.31; 536/24.32; 536/24.33
[58] Field of Search ............... 435/5, 6, 91.1; 536/22.1, 24.3, 24.33

[56] References Cited

U.S. PATENT DOCUMENTS

| | | | |
|---|---|---|---|
| 4,775,619 | 10/1988 | Urdea et al. | 435/6 |
| 4,868,105 | 9/1989 | Urdea et al. | 435/6 |
| 4,910,300 | 3/1990 | Urdea et al. | 536/287 |
| 5,118,605 | 6/1992 | Urdea et al. | 435/6 |
| 5,124,246 | 6/1992 | Urdea et al. | 435/6 |
| 5,256,549 | 4/1990 | Urdea et al. | 435/91.1 |
| 5,258,506 | 11/1993 | Urdea et al. | 435/6 |

Primary Examiner—W. Gary Jones
Assistant Examiner—Dianne Rees
Attorney, Agent, or Firm—Reed & Robins; Kenneth M. Goldman; Robert P. Blackburn

[57] ABSTRACT

Novel N-4 modified pyrimidine analogs are provided having the structure (I) or (II)

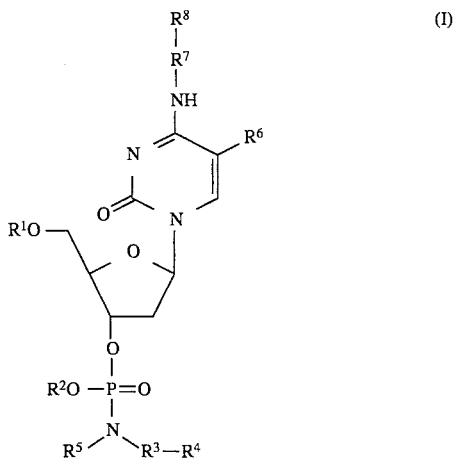

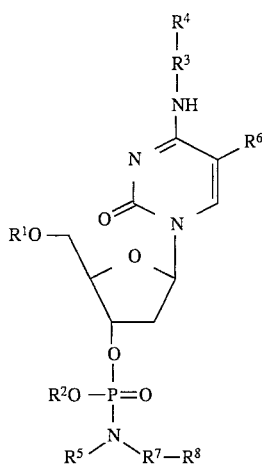

wherein: $R^1$ is selected from the group consisting of hydrogen, acid-sensitive, base-stable blocking groups and acyl capping groups; $R^2$ is lower alkyl; $R^3$ is $C_1$–$C_{12}$ alkylene containing 0 to 6 linkages selected from the group consisting of —O—, —S— and —NH—; $R^4$ is

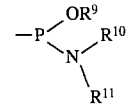

in which $R^9$ is hydrogen or an optionally substituted aliphatic group; $R^{10}$ and $R^{11}$ are hydrocarbyl or together form a mono- or polyheterocyclic ring; $R^5$ is hydrogen or lower alkyl; $R^6$ is selected from the group consisting of hydrogen, methyl, bromo and iodo; $R^7$ is $C_1$–$C_{12}$ alkylene containing 0 to 6 linkages selected from the group consisting of —O—, —S— and —NR$^{12}$— wherein $R^{12}$ is hydrogen or lower alkyl; and $R^8$ is a protecting group that can be removed and replaced by reduction. Synthetic methods for preparing the compounds are provided as well, as are methods for making and using polynucleotide probes containing the novel pyrimidine analogs.

27 Claims, No Drawings

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 11..15
        ( D ) OTHER INFORMATION: /product="N represents compound 5
            or compound 15"

( x i ) SEQUENCE DESCRIPTION: SEQ ID NO:1:

TTTTTTTTTT NNNNN     15

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 11..15
        ( D ) OTHER INFORMATION: /product="N represents compound 5
            or compound 15"

( x i ) SEQUENCE DESCRIPTION: SEQ ID NO:2:

TTTTTTTTTT NNNNNTTTTT TTTTTTTTTT     30

( 2 ) INFORMATION FOR SEQ ID NO:3:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 11..13
        ( D ) OTHER INFORMATION: /product="N represents compound
            15"

( x i ) SEQUENCE DESCRIPTION: SEQ ID NO:3:

TTTTTTTTTT NNN     13

N-4 MODIFIED PYRIMIDINE DEOXYNUCLEOTIDES AND OLIGONUCLEOTIDE PROBES SYNTHESIZED THEREWITH

TECHNICAL FIELD

The invention relates generally to modified nucleotides for incorporation into polynucleotide structures, and more particularly concerns novel N-4 modified pyrimidine-based deoxynucleotides. The invention also relates to polynucleotides containing the novel compounds, to methods of synthesizing the polynucleotides, and to methods of using the polynucleotides in hybridization assays and other contexts.

BACKGROUND

Nucleotidic structures comprising N-4 derivatized pyrimidines have recently been discovered to be extremely useful in the chemical synthesis of linear and branched polynucleotide probes. For example, commonly assigned U.S. Pat. No. 4,910,300 to Urdea et al. describes probes made with modified nucleotides having the structure

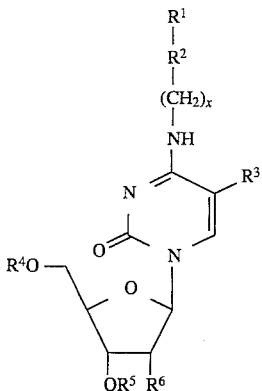

wherein $R^1$ is a reactive group derivatizable with a detectable label, $R^2$ is an optional linking group, $R^3$ is hydrogen, methyl or halogen, $R^4$ is hydrogen or a capping or blocking group, $R^5$ is hydrogen or a phosphorus derivative, and $R^6$ is hydrogen or a protected or unprotected hydroxyl group. The polynucleotide probes described in the '300 patent are linear probes useful in a wide variety of hybridization assay formats, including that involving multi-component capturing and labelling systems as described in commonly assigned U.S. Pat. No. 4,868,105 to Urdea et al.

Such N-4 modified pyrimidine nucleotides have also been used to make branched polynucleotides, as described, for example, in commonly assigned U.S. Pat. No. 5,124,246 to Urdea et al. and in commonly assigned U.S. patent application Ser. No. 07/813,588 ("Large Comb-Type Branched Polynucleotides", inventors Urdea et al.). Both of these documents illustrate the utility of N-4 modified pyrimidine nucleotides in the synthesis of "nucleic acid multimers" or "amplification multimers," polynucleotides having a branched structure by virtue of containing three or more oligonucleotide units emanating from a single point of origin.

The present invention is directed to a new class of N-4 modified pyrimidine nucleotides useful in a variety of contexts, including the hybridization assays described in the aforementioned references. The new compounds may be readily synthesized using commercially available materials, are easily incorporated into polynucleotide probes using conventional synthetic methods, and lend themselves to use in conjunction with automated DNA synthesis equipment.

SUMMARY OF THE INVENTION

Accordingly, the invention in one aspect provides novel compounds useful, inter alia, in the preparation of polynucleotide probes. The novel compounds are modified deoxynucleotides having the structure (I) or (II)

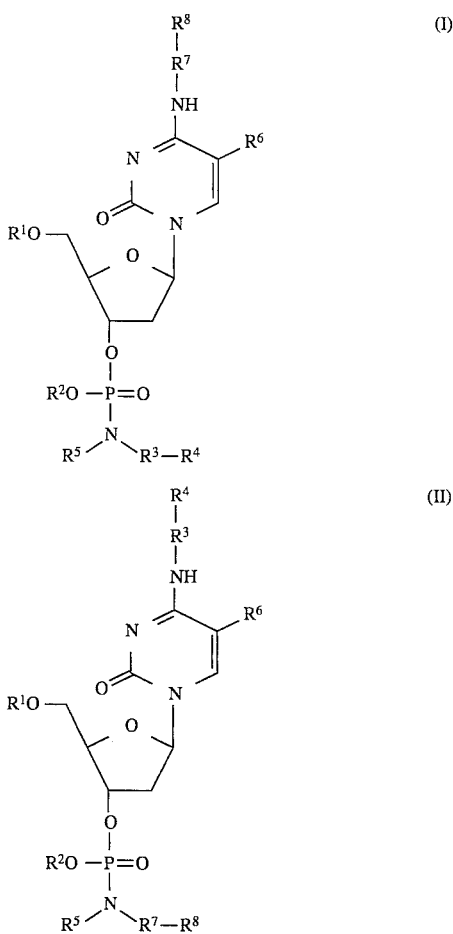

wherein:

$R^1$ is selected from the group consisting of hydrogen, acid-sensitive, base-stable blocking groups and acyl capping groups;

$R^2$ is lower alkyl;

$R^3$ is $C_1$–$C_{12}$ alkylene containing 0 to 6 linkages selected from the group consisting of —O—, —S— and —$NR^{12}$—, bound to $R^4$ through an —O—, —S— or —$NR^{12}$— moiety, where $R^{12}$ is hydrogen or lower alkyl;

$R^4$ is

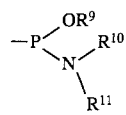

in which $R^9$ is preferably hydrogen or an optionally substituted aliphatic group, and $R^{10}$ and $R^{11}$ are hydrocarbyl or may together form a mono- or polyheterocyclic ring;

$R^5$ is hydrogen or lower alkyl;

$R^6$ is selected from the group consisting of hydrogen, methyl, bromo and iodo;

$R^7$ is $C_1$–$C_{12}$ alkylene containing 0 to 6 linkages selected from the group consisting of —O—, —S— and —$NR^{12}$—, and bound to $R^8$ through an —O—, —S— or —$NR^{12}$— moiety; and $R^8$ is a protecting group that can be removed and replaced, without affecting the remainder of the compound, by reduction with a reducing agent.

In another aspect of the invention, linear polynucleotide probes are provided which contain the modified nucleotides at predetermined, spaced apart positions. The probes are such that the $R^8$ moiety has been replaced with a detectable label; with type (I) compounds, the label will thus be present at the N-4 position, while with type (II) compounds, the label will be present at the 3' position. In a related aspect of the invention, branched polynucleotide probes are provided containing the N-4 modified pyrimidine nucleotides of the invention. The modified nucleotides serve as the branch points by virtue of binding oligonucleotide chains at the N-4 position of the pyrimidine moiety as well as at the 3' and 5' positions of the pentafuranose ring.

In a further aspect of the invention, methods are provided for making polynucleotide probes. Linear probes are prepared by sequentially adding individual nucleotides to a growing oligonucleotide chain, wherein a predetermined fraction of the nucleotides are the modified nucleotides of the invention. The probe is then labelled by replacing the $R^8$ moiety with a detectable label as will be described in detail below. Branched polynucleotide probes are prepared by sequentially adding individual nucleotides to three oligonucleotide chains linked at a single point of origin comprising an N-4 modified pyrimidine nucleotide of the invention. In still other, related aspects of the invention, methods for using the novel probes are provided as well.

In still a further aspect of the invention, such methods are provided for making polynucleotide probes which additionally include introduction of cleavable and/or abasic sites into the probe backbone. The cleavable sites may be enzymatically, chemically or photolytically cleavable, as described in U.S. Pat. Nos. 4,775,619, 5,118,605, 5,258,506 and U.S. patent applications Ser. Nos. 07/736,445 and 07/806,642, all of which are assigned to Chiron Corporation, Emeryville, Calif., and the disclosures of which are incorporated by reference herein. The abasic sites are nonnucleotidic sites as described in U.S. patent application Ser. No. 07/559,961, the disclosure of which is also incorporated by reference. By "abasic site" is meant a monomeric unit contained within a polynucleotide chain but which does not contain a purine or pyrimidine base. The monomeric units used in conjunction with the method of the invention to provide abasic sites contain the deoxyribose ring but do not have a purine or pyrimidine base present at the 1' position.

DETAILED DESCRIPTION OF THE INVENTION

Definitions and nomenclature:

Before the present invention is disclosed and described in detail, it is to be understood that this invention is not limited to specific probe structures, or to specific assay formats, materials or reagents, as such may vary. It is also to be understood that the terminology used herein is for the purpose of describing particular embodiments only and is not intended to be limiting.

In this specification and in the claims which follow, reference will be made to a number of terms which shall be defined to have the following meanings:

As used herein, the terms "polynucleotide" and "oligonucleotide" shall be generic to polydeoxynucleotides (containing 2-deoxy-D-ribose), to polyribonucleotides (containing D-ribose), to any other type of polynucleotide which is an N-glycoside of a purine or pyrimidine base, and to other polymers containing nonnucleotidic backbones (e.g., protein nucleic acids and synthetic sequence-specific nucleic acid polymers commercially available from the Anti-Gene Development Group, Corvallis, Oreg., as Neugene ® polymers), providing that the polymers contain nucleobases in a configuration which allows for base pairing and base stacking, such as is found in DNA and RNA. There is no intended distinction in length between the term "polynucleotide" and "oligonucleotide," and these terms will be used interchangeably. These terms refer only to the primary structure of the molecule. Thus, these terms include double- and single-stranded DNA, as well as double- and single-stranded RNA and DNA:RNA hybrids, and also include known types of modifications, for example, labels which are known in the art, methylation, "caps," substitution of one or more of the naturally occurring nucleotides with an analog, inter-nucleotide modifications such as, for example, those with uncharged linkages (e.g., methyl phosphonates, phosphotriesters, phosphoramidates, carbamates, etc.) and with charged linkages (e.g., phosphorothioates, phosphorodithioates, etc.), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

It will be appreciated that, as used herein, the terms "nucleoside" and "nucleotide" will include those moieties which contain not only the known purine and pyrimidine bases, but also other heterocyclic bases which have been modified. Such modification include methylated purines or pyrimidines, acylated purines or pyrimidines, or other heterocycles. Modified nucleosides or nucleotides will also include modifications on the sugar moiety, e.g., wherein one or more of the hydroxyl groups are replaced with halogen, aliphatic groups, or are functionalized as ethers, amines, or the like.

The term "polynucleotide analyte" refers to a single- or double-stranded nucleic acid molecule which contains a target nucleotide sequence. The analyte nucleic acids may be from a variety of sources, e.g., biological fluids or solids, food stuffs, environmental materials, etc., and may be prepared for the hybridization analysis by a variety of means, e.g., proteinase K/SDS, chaotropic salts, or the like. The term "polynucleotide analyte" is used interchangeably herein with the terms "analyte, " "analyte nucleic acid," "target" and "target molecule."

As used herein, the term "target region" or "target nucleotide sequence" refers to a probe binding region contained within the target molecule. The term "target sequence" refers to a sequence with which a probe will form a stable hybrid under desired conditions.

As used herein, the term "probe" refers to a structure comprised of a polynucleotide, as defined above, which contains a nucleic acid sequence complementary to a nucleic acid sequence present in the target molecule. The polynucleotide regions of probes may be composed of DNA, and/or RNA, and/or synthetic nucleotide analogs.

"Label probe extender molecules (LE's)," also referred to herein as "label extender molecules" or "label extenders," contain regions of complementarity with respect to the analyte polynucleotide and an amplifying multimer as will be described below. If a preamplifier, or mediator probe, is used, the label extenders will bind to such an intermediate species rather than directly to the amplifying multimer. Thus, label extender molecules are single-stranded polynucleotide chains having a first nucleic acid sequence L-1 complementary to a sequence of the analyte polynucleotide, and a second region having a multimer recognition sequence L-2 complementary to a segment M-1 of either the amplification multimer or a preamplifier probe.

"Label probes (LP's)" are designed to bind to the repeating oligonucleotide units of the multimer (or to the preamplifier, if one is used) and either contain a label or are structured so as to bind to a label. Thus, LP's contain a nucleic acid sequence L-3 complementary to a nucleic acid sequence M-2 present within the repeating oligonucleotide units of the multimer and are bound to, or structured so as to bind to, a label which provides, directly or indirectly, a detectable signal.

"Capture extender molecules (CE's)," also referred to herein as "capture extenders," bind to the analyte polynucleotide and to capture probes, which are in turn bound to a solid support. Thus, capture extender molecules are single-stranded polynucleotide chains having a first polynucleotide sequence region containing a nucleic acid sequence C-1 which is complementary to a sequence of the analyte, and a second, noncomplementary region having a capture probe recognition sequence C-2. The sequences C-1 and L-1 are nonidentical, noncomplementary sequences that are each complementary to physically distinct sequences of the analyte.

"Capture probes (CP's)" bind to the capture extenders and to a solid support. Thus, as illustrated in FIG. 1, capture probes have a nucleic acid sequence C-3 complementary to C-2 and are covalently bound to (or capable of being covalently bound to) a solid support.

The terms "nucleic acid multimer" or "amplification multimer" are used herein to refer to a linear or branched polymer of the same repeating single-stranded oligonucleotide unit or different single-stranded polynucleotide units, each of which contains a region where a label probe can bind, i.e., contains a nucleic acid sequence complementary to a nucleic acid sequence contained within a label probe; the oligonucleotide units may be composed of RNA, DNA, modified nucleotides or combinations thereof. Linear multimers contain the N-4 modified pyrimidines of the invention at predetermined, spaced apart positions. With respect to branched amplification multimers, some or all of the "branch points" therein may be formed from the novel compounds, and the multimer may contain additional N-4 modified pyrimidines throughout the linear oligonucleotide segments of the multimer. At least one of the units has a sequence, length and composition that permits it to bind specifically to a segment of a target polynucleotide; typically, such units will contain approximately 15 to 50, preferably 15 to 30, nucleotides, and will have a GC content in the range of about 20% to about 80%. The total number of oligonucleotide units in the multimer will usually be in the range of about 3 to 1000, more typically in the range of about 10 to 100, and most typically about 50. The oligonucleotide units of the multimer may be covalently linked directly to each other through phosphodiester bonds or through interposed linking agents such as nucleic acid, amino acid, carbohydrate or polyol bridges, or through other cross-linking agents that are capable of cross-linking nucleic acid or modified nucleic acid strands.

A "preamplifier" molecule serves as a bridging moiety between the label extender molecules and the amplification multimers. In this way, more amplifier and thus more label is bound in any given target-probe complex. Preamplifier molecules may be either linear or branched, and typically contain in the range of about 200 nucleotides.

By "protecting group" as used herein is meant a species which prevents a segment of a molecule from undergoing a specific chemical reaction, but which is removable from the molecule following completion of that reaction This is in contrast to a "capping group, " which permanently binds to a segment of a molecule to prevent any further chemical transformation of that segment.

The Novel Compounds

The novel modified deoxynucleotides of the invention are represented by structural formulae (I) and (II).

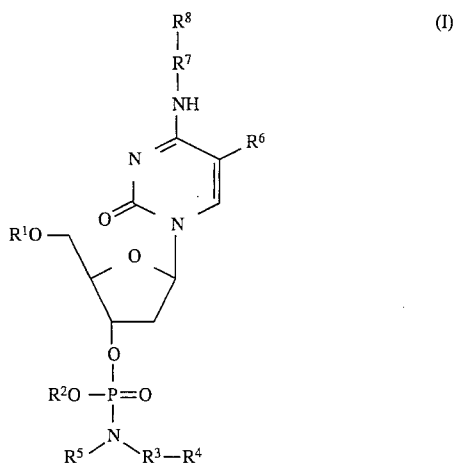

(I)

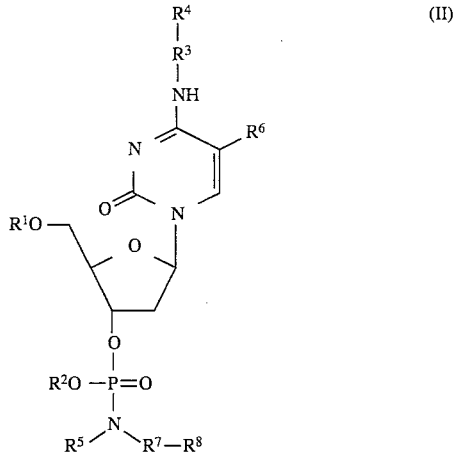

(II)

In the formulae:

$R^1$ is selected from the group consisting of hydrogen, acid-sensitive, base-stable blocking groups and acyl capping groups. Typical blocking groups useful in polynucleotide synthesis and thus preferred for $R^1$ include, but are not limited to, substituted and unsubstituted aralkyl compounds, where the aryl is, e.g., phenyl, naphthyl, furanyl, biphenyl, or the like, and where the substituents are from 0 to 3, usually 0 to 2, and include any non-interfering stable groups, neutral or polar, electron-donating or withdrawing, generally being of 1 to 10, usually 1 to 6, atoms, and generally of from 0 to 7 carbon atoms, and may be an aliphatic, alicyclic, aromatic or heterocyclic group, generally aliphatically saturated, halohydrocarbon, e.g., trifluoromethyl, halo, thioether, oxyether, ester, amide, nitro, cyano, sulfone, amino, azo, etc. Exemplary base-stable blocking groups are dimethoxytrityl, monomethoxytrityl and trityl.

In one or more steps during nucleotide chain synthesis, it may be desirable to replace the hydrogen atom or blocking group at the Rposition with a more stable, "capping" group. Suitable capping groups include acyl groups which provide for stable esters. The acyl groups may be organic or inorganic, including carboxyl, phosphoryl, pyrophosphoryl, and the like. Of particular interest are the alkanoic acids, more particularly aryl-substituted alkanoic acids, where the acid is at least 4 carbon atoms and not more than about 12 carbon atoms, usually not more than about 10 carbon atoms, with the aryl, usually phenyl, substituted alkanoic acids usually of from 8 to 12 carbon atoms. Various heteroatoms may be present such as oxygen (oxy), halogen, nitrogen, e.g., cyano, etc. In general, the carboxylic acid esters will be base labile, while mildly acid-stable, particularly at moderate temperatures below about 50° C., more particularly, below about 35° C. and at pH's greater than about 2, more particularly greater than about 4.

The $R^1$ position may also be used to attach the modified nucleotide to a support, so as to facilitate the sequential addition of nucleotides to the support-bound pyrimidine analog. Covalent attachment to the support is preferred. When the compound is bound to a solid support at the $R^1$ position, $R^1$ is an anchoring group. Depending on the nature of the support, different functionalities will serve as anchors. For silicon-containing supports, such as silica and glass, substituted alkylsilyl or arylsilyl compounds will be employed to form a siloxane or siloximine linkage. With organic polymers, ethers, esters, amines, amides, sulfides, sulfones and phosphates may find use. For aryl groups, such as polystyrene, halomethylation can be used for functionalization, where the halo group may then be substituted by oxy, thio (which may be oxidized to sulfone), amino, phospho (as phosphine, phosphite or phosphate), silyl or the like. With a diatomaceous earth element (e.g., kieselguhr), activation may be effected by a polyacrylic acid derivative and the active functionality reacted with amino groups to form amine bonds. Polysaccharides may be functionalized with inorganic esters, e.g., phosphate, where the other oxygen serves to link the chain. With polyacrylic acid derivatives, the carboxyl or side chain functionality, e.g., N-hydroxyethyl acrylamide, may be used in conventional ways for joining the linking group.

The substituent $R^2$ is a $C_1$–$C_{12}$ saturated aliphatic group optionally containing 1 to 6 substituents such as halogen, lower alkoxy, or the like. Preferably, $R^2$ is lower alkyl, and most preferably, $R^2$ is methyl.

$R^3$ is $C_1$–$C_{12}$ alkylene containing 0 to 6 linkages selected from the group consisting of —O—, —S— and —NR$^{12}$— wherein $R^{12}$ is hydrogen or lower alkyl. An example of a preferred linking group is —(CH$_2$CH$_2$O)$_m$— where m is 1 or 2, and a particularly preferred linking group is —(CH$_2$CH$_2$O)$_2$—. Generally, $R^3$ is bound to $R^4$ through an —O—, —S— or —NR$^{12}$— linking group.

$R^4$ is

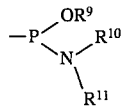

in which $R^9$ is preferably hydrogen or an aliphatic group, particularly a saturated aliphatic group, a β-heterosubstituted aliphatic group, where the β-substituent is an electron-withdrawing group which readily participates in β-elimination, either as the leaving group or the proton-activating group, substituted methylene, where the substituent may vary widely and supports a negative charge on the methylene through inductive or resonating effects; aryl; and aralkyl. Depending on the nature of the phosphorus functionality, one group may be chosen over another. The groups employed for $R^{10}$ and $R^{11}$ may be the same or different and may be hydrocarbon or have from 0 to 5, usually 0 to 4 heteroatoms, primarily oxygen as oxy, sulfur as thio, or nitrogen as amino, particularly tertiary amino, nitro or cyano. $R^{10}$ and $R^{11}$ may be taken together to form a mono-or polyheterocyclic ring having a total of from 1 to 3, usually 1 to 2, heteroannular members having from 1 to 3 rings. Usually, $R^{10}$ and $R^{11}$ will have a total of from 2 to 20, more usually 2 to 16, carbon atoms, where $R^{10}$ and $R^{11}$ may be aliphatic (including alicyclic), particularly saturated aliphatic, monovalent, or, when taken together, divalent radicals, defining substituted or unsubstituted heterocyclic rings. In a particularly preferred embodiment, $R^9$ is methyl or β-cyanoethyl and R and $R^1$ are lower alkyl.

The substituent $R^5$ is hydrogen or lower alkyl, preferably lower alkyl, more preferably methyl.

As noted above, $R^6$ is hydrogen, methyl, bromine, fluorine or iodine. Thus, the base of the nucleotide is a pyrimidine optionally substituted at the 5-position with one of the aforementioned substituents.

$R^7$, like $R^3$, is $C_1$–$C_{12}$ alkylene containing 0 to 6 linkages selected from the group consisting of —O—, —S— and —NR$^{12}$—, wherein $R^{12}$ is as defined previously. Preferably, $R^7$ is —(CH$_2$)$_p$—O— where p is an integer in the range of 1 to 6 inclusive; most preferably, $R^7$ is —(CH)$_6$—O—. $R^7$ is typically bound to $R^8$ through an —O—, —S— or —NR$^{12}$— linking group.

$R^8$ is a protecting group that can be removed and replaced, without affecting the remainder of the compound, by reduction with a liquid reducing agent. Suitable protecting groups are described, for example, in commonly assigned U.S. patent application Ser. No. 07/558,881, the disclosure of which is incorporated by reference herein. Such protecting groups include

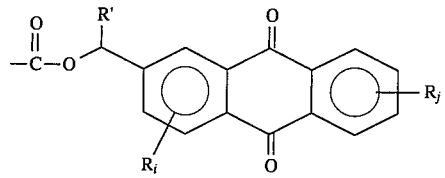

wherein:

R' is hydrogen, aryl or aralkyl; the $R_i$ may be the same or different and are selected from the group consisting of amino, nitro, halogeno, hydroxyl, lower alkyl and lower alkoxy; the $R_j$ may be the same or different and are also selected from the group consisting of amino, nitro, halogeno, hydroxyl, lower alkyl and lower alkoxy; i is zero, 1, 2 or 3; and j is zero, 1, 2, 3 or 4. Another suitable protecting group is

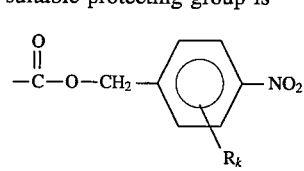

in which k is 0, 1, 2, 3 or 4 and the $R_k$ are independently selected from the group consisting of amino, nitro, halogeno, lower alkyl and lower alkoxy. Still another protecting group suitable as $R^8$ is —(CO)—(CH$_2$)$_n$—COR$^{13}$ where $R^3$ is lower alkyo, preferably methyl, and n is an integer in the range of 1 to 6 inclusive, preferably 2.

An example of a particularly preferred compound having the structural formula (I) is the following:

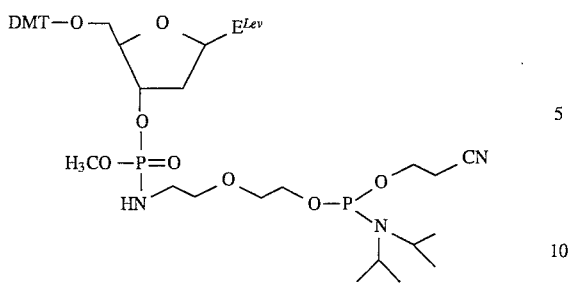

In the above structure, "DMT" represents the dimethoxytrityl substituent, and $E^{Lev}$ is

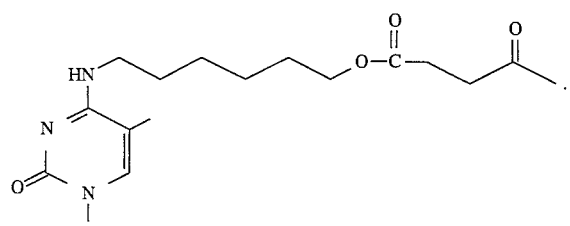

An example of a particularly preferred compound having the structural formula (II) is the following:

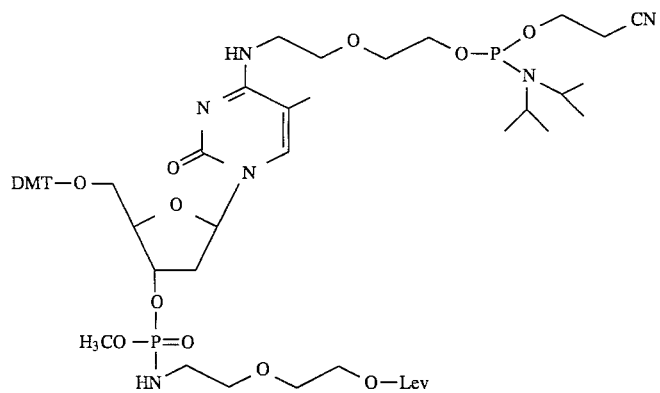

"DMT" is as defined above, and "Lev" represents the levulinyl group

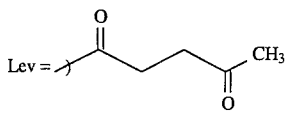

Use of the Novel Compounds in the Synthesis of Polynucleotide Probes

The N-4 modified pyrimidine nucleotides of structural formulae (I) and (II) may be used to synthesize either linear or branched polynucleotide probes. Linear probes may be prepared using the compounds of formula (I) by sequentially adding nucleotides at one or both of the probe termini, such that probes containing recurring units with the structural formula

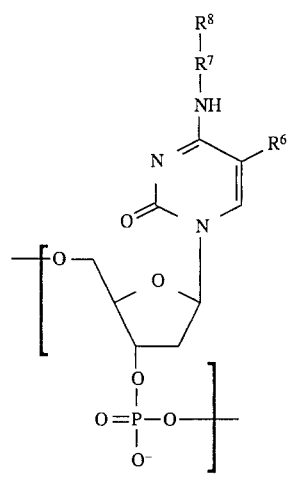

are provided. Linear probes may be prepared using compounds of structural formula (II) by adding nucleotides at the N-4 and 5' positions, such that polynucleotide structures containing recurring units having the formula

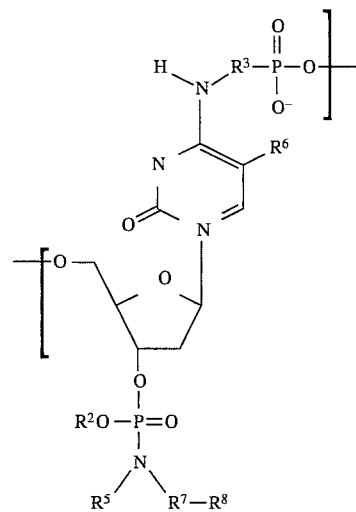

are provided. Nucleotides may be added to the 5' position of either type (I) or type (II) compounds using, for example, the phosphoramidite method of Beaucage and Caruthers, *Tetrahedron Lett.* 22(20):1859–62 (1981) or the phosphotriester method of Itakura et al., *J. Biol. Chem.* 250:4592 (1975), or the like. For compounds having the structural formula (I), nucleotides may be added at the 3' position or at a hydroxyl position present elsewhere, using substantially the same method as described by Belagaje and Brush, *Nuc. Acids Res.* 10:6295 (1982); this method may also be used to add nucleotides to the N-4 position of formula (II)-type compounds.

The general procedure for probe synthesis is as follows. For compounds having the structural formula (I), the blocking group at $R^1$ is removed, and the deprotected compound thus provided is then coupled with a nucleotidic compound having an activated phosphorus group, e.g., a phosphoramidite leaving group, at the 3' position (e.g., a moiety such as that defined above for $R^4$); the coupled product is then oxidized to yield an internucleotidic phosphate moiety, and the process may then be repeated. To prepare probes containing compounds having the structural formula (II), a 5'-blocked nucleotide is provided, and, just prior to coupling, the blocking group at $R^1$ is removed, as above. This compound may then be coupled to an N-4 modified pyrimidine having the structural formula (II), such that the 5' moiety of the starting compound binds to the N-4 position of the formula (II)-type compound, i.e., the $R^4$ moiety is essentially the leaving group in the reaction.

If desired, the linear probes prepared using the present compounds may be labelled at the $R^7$–$R^8$ site by removing $R^8$ and replacing it with a detectable label, e.g., an enzyme, a fluorescer, a chemiluminescer, a radionuclide, an enzyme substrate, a cofactor or suicide inhibitor, a specific binding pair member (e.g., a hapten), or the like. With probes containing type (I) compounds, the label will be at the N-4 position, while with probes containing type (II) compounds, the label will be at the 3' position.

Compounds of formulae (I) and (II) may also be used as branch points in the preparation of branched polynucleotide structures. To use the compounds in this way, nucleotides are added at the 3' position, the 5' position and the N-4 position using the methods as described above. In general, linear probes containing type (I), type (II) compounds, or both, are prepared, followed by attachment of additional nucleotides at the site containing the nitrogen-linked $R^7$–$R^8$ moiety. To effect this additional step, the $R^8$ groups are removed (e.g., when $R^8$ is levulinyl, it may be removed using hydrazine hydrate in a pyridine/glacial acetic acid solution) followed by a coupling step such as described above, i.e., those described by Beaucage and Caruthers (1981) and Itakura (1975)).

It will be appreciated by those skilled in the art that probes constructed using the novel compounds may be used in a wide variety of hybridization assays. A particularly preferred assay with which linear polynucleotide probes constructed with the present compounds may be used is that described in U.S. Pat. No. 4,868,105 to Urdea et al. That assay involves the use of a two-part capturing system designed to bind the polynucleotide analyte to a solid support, and a two-part labeling system designed to bind a detectable label to the polynucleotide analyte to be detected or quantitated. The two-part capture system involves the use of capture probes bound to a solid support and capture extender molecules which hybridize both to a segment of the capture probes and to a segment of the polynucleotide analyte. The two-part labelling system involves the use of label extender molecules which hybridize to a segment of the polynucleotide analyte, and label probes which hybridize to the label extender molecules and contain or bind to a detectable label. An advantage of such a system is that a plurality of hybridization steps must occur in order for label to be detected in a manner that correlates with the presence of the analyte, insofar as two distinct hybridization reactions must occur for analyte "capture," and similarly, two distinct hybridization reactions must occur for analyte labelling. Any of the aforementioned probes may contain N-4 modified pyrimidine nucleotides as provided herein, although it is preferred that the novel compounds be incorporated into the label probes, such that labelling sites are provided at either the N-4 or 3' positions (i.e., with type (I) and type (II) compounds, respectively).

A particularly preferred assay with which branched polynucleotide probes constructed with the present compounds may be used is a solution phase sandwich hybridization assay in which, initially, single-stranded analyte nucleic acid is incubated under hybridization conditions with capture extender molecules and label extender molecules. The resulting product is a nucleic acid complex of the analyte polynucleotide bound to the capture extender molecules and to the label extender molecules. This complex is then added under hybridizing conditions to a solid phase having the capture probes bound to the surface thereof; alternatively, and in most cases preferably, the initial incubation is carried out in the presence of the support-bound capture probes. The resulting product comprises the complex bound to the solid phase via the capture extender molecules and capture probes. The solid phase with bound complex is then separated from unbound materials. The amplification multimer, constructed using type (I) and/or type (II) compounds to provide for branch points, is then added to the solid phase-analyte-probe complex under hybridization conditions to permit the multimer to hybridize to the label extender molecules; if preamplifier probes are used, the solid phase-analyte-probe complex is incubated with the preamplifier probes either along with the amplification multimer or prior to incubation with the amplification multimer. The incubation with the amplification multimer. The resulting solid phase complex is then separated from any unbound preamplifier and/or multimer by washing. The label probes are then added under conditions which permit hybridization to the repeating oligonucleotide units of the multimer. The resulting solid phase labeled nucleic acid complex is then washed to remove unbound labeled oligonucleotide, and read.

Synthesis of Type (I) and Type (II) Compounds

The following schemes illustrate preferred protocols for preparing the compounds of the invention, with Scheme I directed to preparation of type (I) compounds and Scheme II directed to preparation of type (II) compounds:

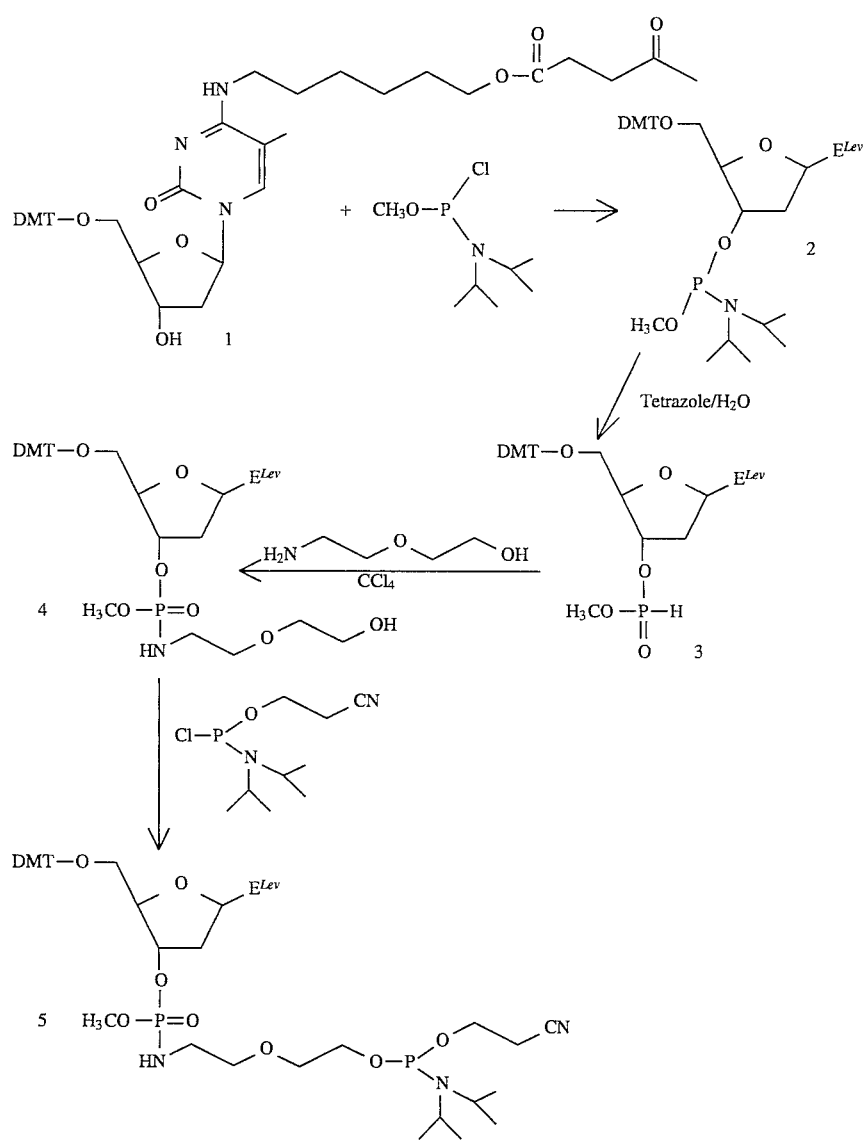
Scheme I
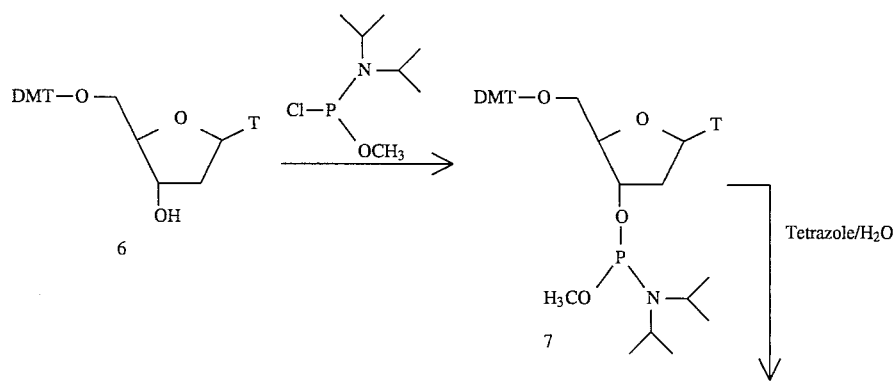
Scheme II

-continued
Scheme II

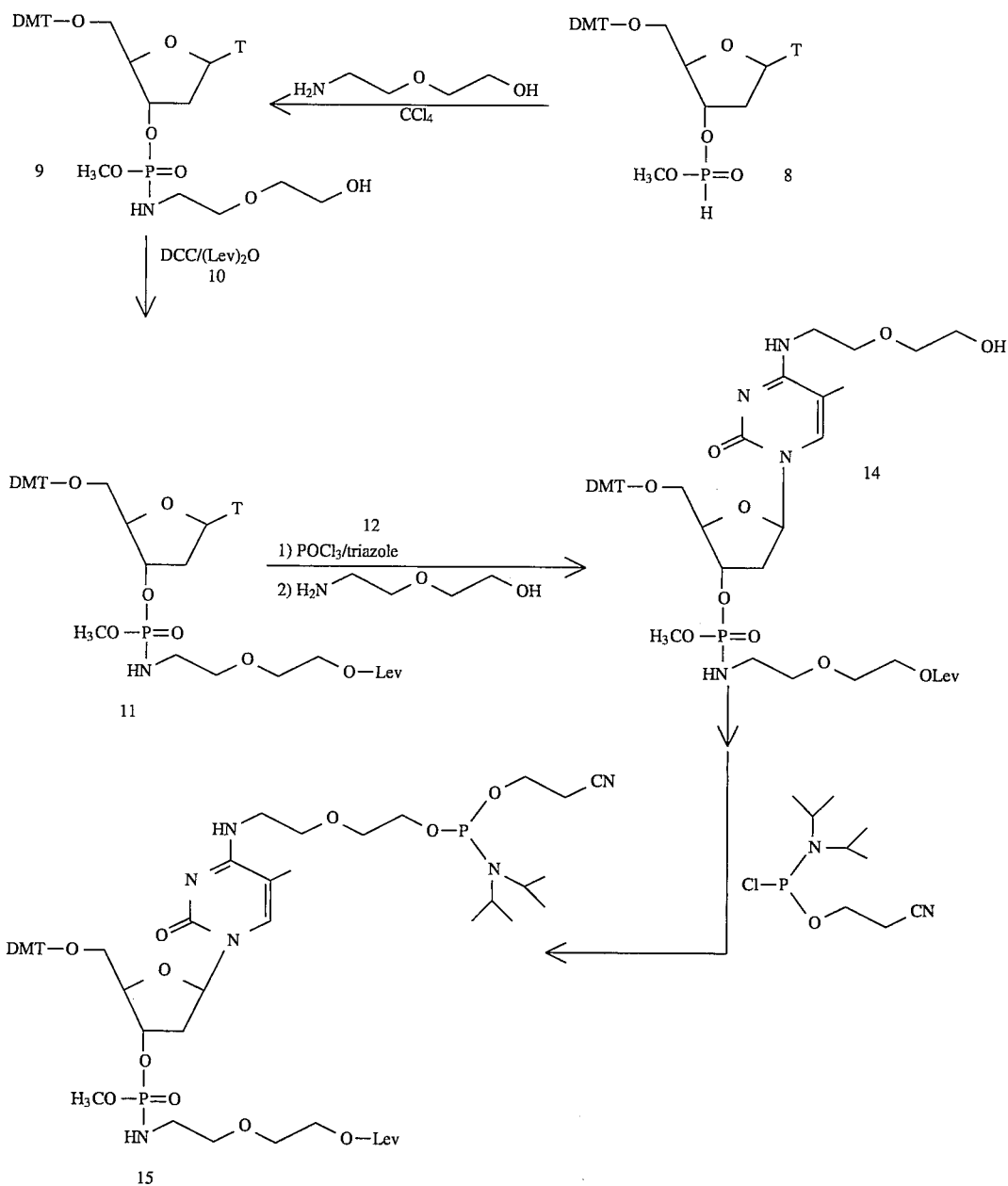

In Scheme I, the starting material 1 is a 5'-protected pyrimidine containing the levulinyl group bound through an alkylene chain to the N-4 position of the pyrimidine ring (with respect to structure (I), $R^7$ is —$(CH_2)_6$— and $R^8$ is —(CO)—$CH_2CH_2$—$COCH_3$). Such a compound may be prepared using any number of techniques which are well known to those skilled in the art of oligonucleotide synthesis. The 5' hydroxyl is coupled with an amino-containing phosphine to provide the 3'-phosphoramidite 2, followed by oxidation to the H-phosphonate 3. The phosphonate moiety of compound 3 is then caused to react with 2-(2-aminoethyl)ethanol to provide for a —NH—$(CH_2)_2$—O—$(CH_2)_2$—OH group bound to the phosphorus at the 3' position in compound 4, followed by an additional coupling step with chloro(diisopropylamino)-β-cyanoethylphosphine to yield the product 5.

In Scheme II, a 5'-protected thymidine (compound 6, which may be obtained from Chem-Impex International, Inc., Wood Dale, Ill. [cat. #00134]) serves as the starting material, and is reacted with an amino-containing phosphine, as in Scheme I, to provide the 3'-phosphoramidite 7, followed by oxidation to the H-phosphonate 8. As in Scheme I, the H-phosphonate 8 is caused to react with 2-(2-aminoethyl)ethanol to provide for a —NH—$(CH_2)_2$—O—$(CH_2)_2$—OH group bound to the phosphorus at the 3' position in compound 9. At this point, the terminal hydroxyl group extending from the 3' position is coupled to the levinylinyl group (in compound 11), followed by reaction at the N-4 position to provide for an N-4 linked —$(CH_2)_2$—O—$(CH_2)_2$—OH moiety in compound 14. As in the final step of Scheme I, the terminal hydroxyl group, in this case at N-4, is caused to react with chloro-(diisopropylamino)-β-cyanoethylphosphine to yield the product 15.

It will be appreciated that the specific compounds shown in the schemes are for purposes of illustration only, and that other types of blocking groups (i.e., at $R^1$), linking moieties (i.e., at $R^3$ and $R^7$), terminal groups (i.e., at $R^4$ and $R^8$) and other substituents (e.g., $R^2$, $R^5$, and $R^6$) may be substituted as explained in the preceding section.

Examples 1 and 2 set forth the experimental detail supporting the above description of the reaction schemes.

Other Uses

In addition to their utility in the preparation of polynucleotide probes, the compounds of the invention may be used in conjunction with other types of compounds that are useful for creating selectably cleavable sites in polynucleotide chains and/or for creating abasic sites. See, e.g., those patents and applications cited and incorporated by reference above, namely, U.S. Pat. Nos. 4,775,619, 5,118,605, 5,258,506 and U.S. patent applications Ser. Nos. 07/559,961, 07/736,445 07/806,642. As explained in the aforementioned patents and applications, a number of reagents and methods may be used to create abasic sites and/or sites which are cleavable using chemical reagents, restriction enzymes or photolysis. The compounds of the invention may themselves be useful in creating cleavable sites, i.e., sites which by virtue of the phosphoramidite moiety are acid-labile and thus may be cleaved by treatment with acid. Generally, "cleavable" sites are used to release a detectable label following completion of a hybridization assay, the presence and/or quantity of label being indicative of the presence and/or quantity of analyte.

Experimental

The practice of the present invention will employ, unless otherwise indicated, conventional techniques of synthetic organic chemistry, biochemistry, molecular biology, and the like, which are within the skill of the art. Such techniques are explained fully in the literature. See, e.g., Sambrook, Fritsch & Maniatis, *Molecular Cloning: A Laboratory Manual*, Second Edition (1989); *Oligonucleotide Synthesis* (M. J. Gait, ed., 1984); *Nucleic Acid Hybridization* (B. D. Hames & S. J. Higgins, eds., 1984); and a series, *Methods in Enzymology* (Academic Press, Inc.). All patents, patent applications, and publications mentioned herein, both supra and infra, are hereby incorporated by reference.

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will be apparent to those skilled in the art to which the invention pertains.

In the following examples, efforts have been made to insure accuracy with respect to numbers used (e.g., amounts, temperature, etc.) but some experimental error and deviation should be accounted for. Unless indicated otherwise, temperature is in degrees C. and pressure is at or near atmospheric.

EXAMPLE 1

Preparation of compound 5 (Scheme I)

(a.) Preparation of E(Lev)-methylphosphoramidite 2:

Into a cold solution (0° C.) of DMT-E(Lev)—OH 1 (4.52 g, 6.1 mmol) in 30 mL $CH_2Cl_2$ and 5.3 mL diisopropylethylamine (DIPEA) (30.5 mmol) was added chloro (diisopropylamino)-methoxyphosphine (1.2 mL, 6.1 mmol) dropwise. The ice bath was removed at the end of addition. TLC showed complete disappearance of the starting material after 30 min. The reaction mixture was first diluted with 400 mL ethyl acetate, followed by partitioned once with 400 mL of 5% $NaHCO_3$ (aq) and twice with 400 mL of 80% NaCl(aq). The organic phase was separated and dried over anhydrous $Na_2SO_4$ before filtering. The volatile solvents were removed under vacuum and the residue was coevaporated with toluene (100 mL) and acetonitrile (100 mL), respectively, to dryness. The product was a white foam, weighed 5.7 g and used without further purification.

(b.) Hydrolysis of 2 to E(lev)-methyl-H-phosphonate 3:

Into the solution of 2 in 75 mL acetonitrile was added tetrazole (0.88 g, 12.6 mmol) in 50 mL acetonitrile and 1 mL $H_2O$. The reaction was completed in 15 min at room temp as indicated by TLC. The product was worked up by the same procedure as described above in part (a.). After drying, the product weighed 5.5 g as a white foam and was used without further purification.

(c.) Conversion of 3 to 4:

A solution of 2-(2-aminoethyl)ethanol (7.4 g, 70 mmol) in 30 mL carbon tetrachloride and 30 mL acetonitrile was added dropwise to a solution of 3 (5.8 g) in 100 mL acetonitrile. The reaction was completed after stirring for 2 hr at room temp. The reaction mixture was first reduced to 25 mL under vacuum before diluted with 500 mL ethyl acetate. The workup procedure was the same as that described above with respect to part (a.). The oily product weighed 5.4 g and was used without further purification.

(d.) Phosphitylation of 4:

Into the solution of 4 in 30 mL $CH_2Cl_2$ and DIPEA (5.1 mL, 29.5 mmol) at 0° C. was added dropwise the chloro-(diisopropylamino)-β-cyanoethylphosphine (1.56 mL, 7.1 mmol). The reaction was stirred at room temp for 30 min before being worked up as described in part (a.). The product was further purified by flash silica chromatography using increasing triethyl-amine (TEA) gradient in $CH_2Cl_2$. The desired product fractions were pooled and dried under vacuum. The product 5 was further coevaporated twice with anhydrous acetonitrile (2×100 mL) and weighed 3.9 g (3.5 mmol).

EXAMPLE 2

Preparation of Compound 12 (Scheme II).

(a.) Synthesis of DMT-T-methylphosphoramidite 7:

To a cold solution (ice bath) of DMT-T 6 (10.89 g, 20 mmol) in 45 mL $CH_2Cl_2$ and DIPEA (17.4 mL, 100 mmol) was added chloro(diisopropylamino)methoxyphosphine (7.1 mL, 36.7 mmol). The reaction was worked up, after stirring for 1 hr at room temp, by diluting with 700 mL ethyl acetate. The organic phase was then partitioned once with 700 mL 5% $NaHCO_3$(aq) and twice with 80% NaCl(aq) (2×700 mL). The drying and coevaporating was the same as above. The product, weighed 17.22 g, was a white foam and used without further purification.

(b.) Hydrolysis of to its H-phosphonate analog 8:

Into the solution of 7 in 200 mL acetonitrile was added tetrazole (3.42 g, 48.8 mmol) in 110 mL acetonitrile and 3 mL $H_2O$ at room temp. The reaction, completed in 15 min as indicated by TLC, was worked up using the same procedure as described above. The product 8 was a white foam, weighed 15.7 g, and used without further purification.

(c.) Conversion of to 8 to 9:

Into the solution of 8 in 200 mL acetonitrile and 100 mL carbon tetrachloride at room temp was added the 2-(2-aminoethyl)ethanol in 100 mL $CH_3CN$. The mixture was stirred for 1 hr at room temp and worked up using the same procedure as in 1. The product 9 was a white foam, weighed 17.3 g, and used without further purification.

(d.) Preparation of levulinic anhydride 10:

Into a solution of levulinic acid (23.2 g, 200 mmol) in 400 mL THF was added dropwise the dicyclohexylcarbodiimide (DCC, 21.1 g, 100 mmol) in 100 mL THF at room temp. The precipitate was filtered out after 5 hr and the supernatant was stored in a 4° C. refrigerator.

(e.) Levulinylation of 9 to 11:

Into a THF solution (50 mL) of (5.8 g) was added 100 mL of the above levulinic anhydride solution 10 with stirring. Ten milliliter of a DMAP solution (6.5% (w/v) in THF/lutidine, 9:1, v/v). The reaction was stirred overnight at room temp. The reaction mixture was first reduced to 25 mL and then diluted with 600 mL ethyl acetate. Aqueous workup was the same as above. After dried under vacuum, the product weighed 7.8 g and was used without further purification.

(f.) Preparation of phosphorus oxytris(triazolide) 12:

Into a cold (ice bath) triazole (9.8 g, 142.5 mmol) solution in 100 mL $CH_3CN$ was added phosphorus oxychloride (3 mL, 33.3 mmol) dropwise, followed by 24 mL triethylamine. The mixture was stirred for another 30 min at 0° C.

(g.) Conversion of 11 to 13:

Compound 11 was first dissolved in 100 mL $CH_3CN$ and the undissolved residue was filtered out. The filtrate was added dropwise to the above cold solution 12. The bath was removed at the conclusion of addition, and the mixture was stirred for 3 hr at room temp. The reaction was first diluted with 700 mL ethyl acetate and partitioned with 5% $NaHCO_3$(aq) and 80% NaCl(aq) according to the same procedure as previously described. After coevaporation and drying, the product 13 weighed 7.8 g as a light brown oil.

(h.) Derivatization of 13 with 2-(2-aminoethyl)ethanol:

To the solution of 13(7.8 g) in 90 mL $CH_3CN$ was added 1 mL of 2-(2-aminoethyl)ethanol in 20 mL $CH_3CN$ dropwise at room temp. The reaction was stirred for 3 hr before diluted with 600 mL ethyl acetate. Workup procedure was the same as before. The product was obtained as an oil and weighed 7.3 g. The oily product was further purified by flash silica chromatography. The silica gel was prepared in $CH_2Cl_2$/TEA (99:1, v/v) and the product was eluted with an increasing gradient of methanol in the same solvent system. 3.65 g of product 14 was obtained as a white foam.

(i.) Phosphitylation of 14:

Compound 14 (3.65 g) was first dissolved in 30 mL $CH_2Cl_2$ and 3.5 mL DIPEA and the solution was chilled in an ice bath. To this cold solution was added the chloro(diisopropylamino)-β-cyanoethylphosphine (1.15 mL, 5.3 mmol) dropwise. The reaction was stirred for 1 hr and then worked up (following the same procedure as before). A white foam was obtained and weighed 4.85 g. The product was further purified by flash silica chromatography with an increasing gradient of triethylamine. The product fractions were pooled and volatile solvents removed under vacuum. The product 15, after coevaporated with toluene and anhydrous acetonitrile, weighed 2.55 g (2.3 mmol).

EXAMPLE 3

Compounds 5 and 15 were tested for functionality as follows. The coupling efficiencies of the compounds were evaluated by synthesizing an oligonucleotide having the sequence 3'-TTTTTTTTTTRRRRR-5' (SEQ ID NO: 1). In a first case where R was compound 5 and in a second case where R was compound 15. All chemical syntheses of oligonucleotides were performed on an automatic DNA synthesizer (Applied Biosystems, Inc. (ABI) model 380 B). Phosphoramidite chemistry of the cyanoethyl type was used. To generate the solid support, 1400 Å controlled pore glass (CPG) was loaded to 21.2 micromoles/gram with thymidine and protected at the 5' —OH with dimethoxytrityl (DMT), via a long-chain alkylamine linkage. 0.6 micromoles of solid support was placed in a column and washed with acetonitrile. Trichloroacetic acid was added to the derivatized CPG to remove the DMT. Following a wash with acetonitrile, 0.1M thymidine phosphoramidite (10 mg/coupling) and 0.5M tetrazole were added to the column and allowed to react for 20 seconds. Unreacted terminal hydroxyl groups were capped using a mixture of acetic anhydride in the presence of dimethylaminopyridine. The phosphite was then oxidized to phosphate using iodine in tetrahydrofuran solution. After several acetonitrile washes the next round of coupling was initiated with the trichloroacetic acid addition as above. The coupling of each thymidine followed the same protocol. For the compound 5 couplings, the cycle was modified to include 0.2M compound 5-phosphoramidite (34 mg/coupling) and a 5 minute reaction time for coupling. For compound 15 couplings, the cycle was modified to include double condensations of 0.2M compound 15-phosphoramidite (34 mg/coupling, a total of 68 mg used) with a 1.5 minute reaction time after each amidite addition.

The average of the coupling efficiency over the five couplings is listed below.

| Molecule | Coupling Efficiency |
| --- | --- |
| Compound 5 | 91.7% |
| Compound 15 | 99.1% |

It may be deduced from these results that both phosphoramidites couple with high efficiency.

EXAMPLE 4

Construction of Branched DNA

The levulinyl groups of the 3'-TTTTTTTTTTRRRRR-5' (SEQ ID NO: 1) sequences (with R=either compound 5 or compound 15) were removed by treating the CPG support with a solution of 0.5M hydrazine hydrate in pyridine/glacial acetic acid (1:1 v/v) for 90 min at room temperature with renewal of the hydrazine solution every 15 minutes. After extensive wash with acetonitrile, the CPG was put back on the DNA synthesizer. The newly exposed side chain hydroxyl groups were extended with three thymidine bases using standard oligonucleotide synthesis chemistry. Following synthesis, hot concentrated ammonia was used to remove all protecting groups from the branched DNA. High performance capillary electrophoresis of both crude branched DNA showed major product peaks corresponding to the structure 3' TTTTTTTTTTRRRRR[TTT]$_5$5' (SEQ ID NO: 2) where the sequence in the bracket is attached to the side chain of R.

EXAMPLE 5

Acid hydrolysis of 3' TTTTTTTTTTRRRRR[TTT]$_5$5' (SEQ ID NO: 2) (R=compound 15): the branched DNA made with compound 15 was hydrolyzed with 80% aqueous acetic acid at room temperature for 6 hours. HPCE showed 70% conversion of the branched DNA to a faster moving peak which corresponded to the product obtained from the hydrolysis of 3' TTTTTTTTTTRRR5' (SEQ ID NO: 3).

We claim:

1. A modified deoxynucleotide having the structure (I) or (II)

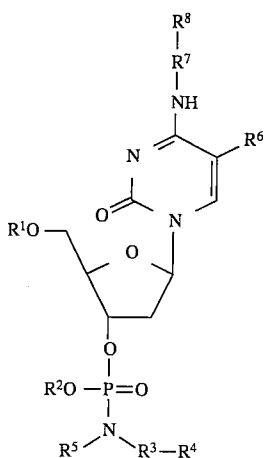 (I)

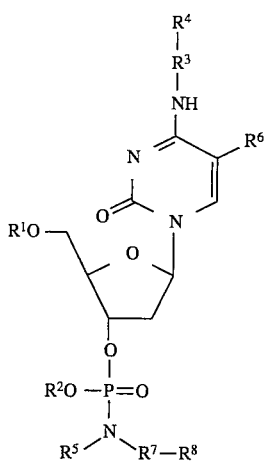 (II)

wherein:

R$^1$ is selected from the group consisting of hydrogen, acid-sensitive, base-stable blocking groups and acyl capping groups;

R$^2$ is lower alkyl;

R$^3$ is C$_1$–C$_{12}$ alkylene containing 0 to 6 linkages, wherein said linkages are selected from the group consisting of —O—, —S— and —NR$^{12}$— and wherein R$^{12}$ is hydrogen or lower alkyl, and bound to R$^4$ through an —O—, —S— or —NR$^{12}$— moiety;

R$^4$ is

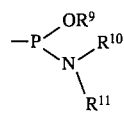

in which R$^9$ is hydrogen or a saturated aliphatic group, and R$^{10}$ and R$^{11}$ are independently selected from hydrocarbyl having from 0 to 5 heteroatoms, or may be taken together to form a mono- or polyheterocyclic ring;

R$^5$ is hydrogen or lower alkyl;

R$^6$ is selected from the group consisting of hydrogen, methyl, bromo and iodo;

R$^7$ is C$_1$–C$_{12}$ alkylene containing 0 to 6 linkages selected from the group consisting of —O—, —S— and —NR$^{12}$—, and bound to R$^8$ through an —O—, —S— or —NR$^{12}$— moiety; and R$^8$ is a protecting group that can be removed and replaced, without affecting the remainder of the compound, by reduction with a reducing agent.

2. The modified deoxynucleotide of claim 1, having the structure (I).

3. The modified deoxynucleotide of claim 2, wherein R$^1$ is dimethoxytrityl.

4. The modified deoxynucleotide of claim 2, wherein R$^2$ is methyl.

5. The modified deoxynucleotide of claim 2, wherein R$^3$ is —(CH$_2$CH$_2$O)$_m$— where m is 1 or 2.

6. The modified deoxynucleotide of claim 5, wherein m is 2.

7. The modified deoxynucleotide of claim 2, wherein R$^4$ is β-cyanoethyl-N,N-diisopropylamino phosphoramidite.

8. The modified deoxynucleotide of claim 2, wherein R$^5$ is hydrogen.

9. The modified deoxynucleotide of claim 2, wherein R$^6$ is methyl.

10. The modified deoxynucleotide of claim 2, wherein R$^6$ is hydrogen.

11. The modified deoxynucleotide of claim 2, wherein R$^7$ is —(CH$_2$)$_p$O— in which p is an integer in the range 1 to 6 inclusive.

12. The modified deoxynucleotide of claim 11, wherein p is 6.

13. The modified deoxynucleotide of claim 2, wherein R$^8$ is —(CO)—CH$_2$CH$_2$—COCH$_3$.

14. The modified deoxynucleotide of claim 2, wherein:

R$^1$ is dimethoxytrityl;

R$^2$ is methyl;

R$^3$ is —(CH$_2$CH$_2$O)$_m$— where m is 1 or 2;

R$^4$ is β-cyanoethyl-N,N-diisopropylamino phosphoramidite;

R$^5$ is hydrogen;

R$^6$ is methyl;

R$^7$ is —(CH$_2$)$_p$—O— where p is an integer in the range of 1 to 6 inclusive; and R$^8$ is —(CO)—CH$_2$CH$_2$—COCH$_3$.

15. The modified deoxynucleotide of claim 1, having the structure (II).

16. The modified deoxynucleotide of claim 15, wherein R$^1$ is dimethoxytrityl.

17. The modified deoxynucleotide of claim 15, wherein R$^2$ is methyl.

18. The modified deoxynucleotide of claim 15, wherein R$^3$ is —(CH$_2$CH$_2$O)$_m$— where m is 1 or 2.

19. The modified deoxynucleotide of claim 18, wherein m is 2.

20. The modified deoxynucleotide of claim 15, wherein R$^4$ is β-cyanoethyl-N,N-diisopropylamino phosphoramidite.

21. The modified deoxynucleotide of claim 15, wherein R$^5$ is hydrogen.

22. The modified deoxynucleotide of claim 15, wherein R$^6$ is methyl.

23. The modified deoxynucleotide of claim 15, wherein R$^6$ is hydrogen.

24. The modified deoxynucleotide of claim 15, wherein R$^7$ is —(CH$_2$)$_p$O— in which p is an integer in the range of 1 to 6 inclusive.

25. The modified deoxynucleotide of claim 24, wherein p is 6.

26. The modified deoxynucleotide of claim 15, wherein R$^8$ is —(CO)—CH$_2$CH$_2$—COCH$_3$.

27. The modified deoxynucleotide of claim 15, wherein:

$R^1$ is dimethoxytrityl;

$R^2$ is methyl;

$R^3$ is —$(CH_2CH_2O)_m$— where m is 1 or 2;

$R^4$ is β-cyanoethyl-N,N-diisopropylamino phosphoramidite;

$R^5$ is hydrogen;

$R^6$ is methyl;

$R^7$ is —$(CH_2)_p$—O— where p is an integer in the range of 1 to 6 inclusive; and $R^8$ is —(CO)—$CH_2CH_2$—$COCH_3$.

* * * * *